(12) United States Patent
Lustig et al.

(10) Patent No.: US 6,786,725 B2
(45) Date of Patent: *Sep. 7, 2004

(54) DENTAL IMPLANT AND TOOL AND METHOD FOR EFFECTING A DENTAL RESTORATION USING THE SAME

(76) Inventors: L. Paul Lustig, 304 Greenwood St., Newton, MA (US) 02159; Federico Castellucci, 719 South Ave., Weston, MA (US) 02193; Andrew P. Tybinkowski, 39 Burning Bush Dr., Boxford, MA (US) 01921

(*) Notice: Subject to any disclaimer, the term of this patent is extended or adjusted under 35 U.S.C. 154(b) by 0 days.

This patent is subject to a terminal disclaimer.

(21) Appl. No.: 09/951,139

(22) Filed: Sep. 12, 2001

(65) Prior Publication Data

US 2002/0110783 A1 Aug. 15, 2002

Related U.S. Application Data

(63) Continuation of application No. 09/193,933, filed on Nov. 17, 1998, now Pat. No. 6,287,115.

(51) Int. Cl.[7] ................................................. A61C 8/00
(52) U.S. Cl. ...................................................... 433/173
(58) Field of Search ................................. 433/172, 173, 433/174, 175, 176

(56) References Cited

U.S. PATENT DOCUMENTS

| | | |
|---|---|---|
| 3,732,621 A | 5/1973 | Bostrom |
| 4,400,160 A | 8/1983 | Lustig et al. |
| 4,575,340 A | 3/1986 | Lustig |
| 4,689,013 A | 8/1987 | Lustig |
| 4,713,004 A | 12/1987 | Linkow et al. |
| 4,793,808 A | 12/1988 | Kirsch |
| 4,832,601 A | 5/1989 | Linden |
| 4,842,518 A | 6/1989 | Linkow et al. |
| 4,854,872 A | 8/1989 | Detsch |
| 4,907,969 A | 3/1990 | Ward |
| 5,015,186 A | 5/1991 | Detsch |
| 5,071,350 A | 12/1991 | Niznick |
| 5,073,110 A | 12/1991 | Barbone |
| 5,116,225 A | 5/1992 | Riera |
| 5,133,662 A | 7/1992 | Metcalfe |
| 5,145,369 A | 9/1992 | Lustig et al. |
| 5,178,539 A | 1/1993 | Peltier et al. |
| 5,195,891 A | 3/1993 | Sulc |
| 5,213,502 A | 5/1993 | Daftary |
| 5,302,125 A | 4/1994 | Kownacki et al. |
| 5,362,235 A | 11/1994 | Daftary |
| 5,564,922 A | 10/1996 | Rosa et al. |
| 5,564,925 A | 10/1996 | Shampanier |
| 5,577,912 A | 11/1996 | Prins |
| 5,599,185 A | 2/1997 | Greenberg |
| 5,658,147 A | 8/1997 | Phimmasone |

(List continued on next page.)

FOREIGN PATENT DOCUMENTS

| | | |
|---|---|---|
| EP | 0 580 945 A1 | 2/1994 |
| EP | 0 288 702 A2 | 11/1998 |

*Primary Examiner*—John J Wilson
(74) *Attorney, Agent, or Firm*—Pandiscio & Pandiscio

(57) ABSTRACT

A novel dental implant comprising an implant fixture assembly for attachment to a jaw bone at a first end thereof, the fixture assembly having a longitudinal axis; an abutment for mounting on a second end of the fixture assembly, the abutment having a longitudinal axis; and a fastener for connecting the abutment to the second end of the implant fixture assembly such that the abutment is movable on the second end of the implant fixture assembly and, upon disposition of the abutment axis at a selected angle to the implant fixture assembly axis, for connecting the abutment to the second end of the implant fixture assembly such that the abutment is fixed on the implant fixture assembly at the selected angle. A novel tool for deploying the novel dental implant is also disclosed. And a novel method for effecting a dental restoration is also disclosed.

3 Claims, 17 Drawing Sheets

U.S. PATENT DOCUMENTS

| | | |
|---|---|---|
| 5,662,475 A | 9/1997 | Mena |
| 5,667,384 A | 9/1997 | Sutter et al. |
| 5,674,069 A | 10/1997 | Osorio |
| 5,674,070 A | 10/1997 | Fortin et al. |
| 5,674,071 A | 10/1997 | Beaty et al. |
| 5,674,072 A | 10/1997 | Moser et al. |
| 5,674,073 A | 10/1997 | Ingber et al. |
| 5,685,714 A | 11/1997 | Beaty et al. |
| 5,688,123 A | 11/1997 | Meiers et al. |
| 5,692,904 A | 12/1997 | Beaty et al. |
| 5,695,334 A | 12/1997 | Blacklock et al. |
| 5,695,335 A | 12/1997 | Haas et al. |
| 5,695,337 A | 12/1997 | Tyszblat Sadoun |
| 5,704,788 A | 1/1998 | Milne |
| 5,711,669 A | 1/1998 | Hurson |
| 5,810,591 A | 9/1998 | Huber |

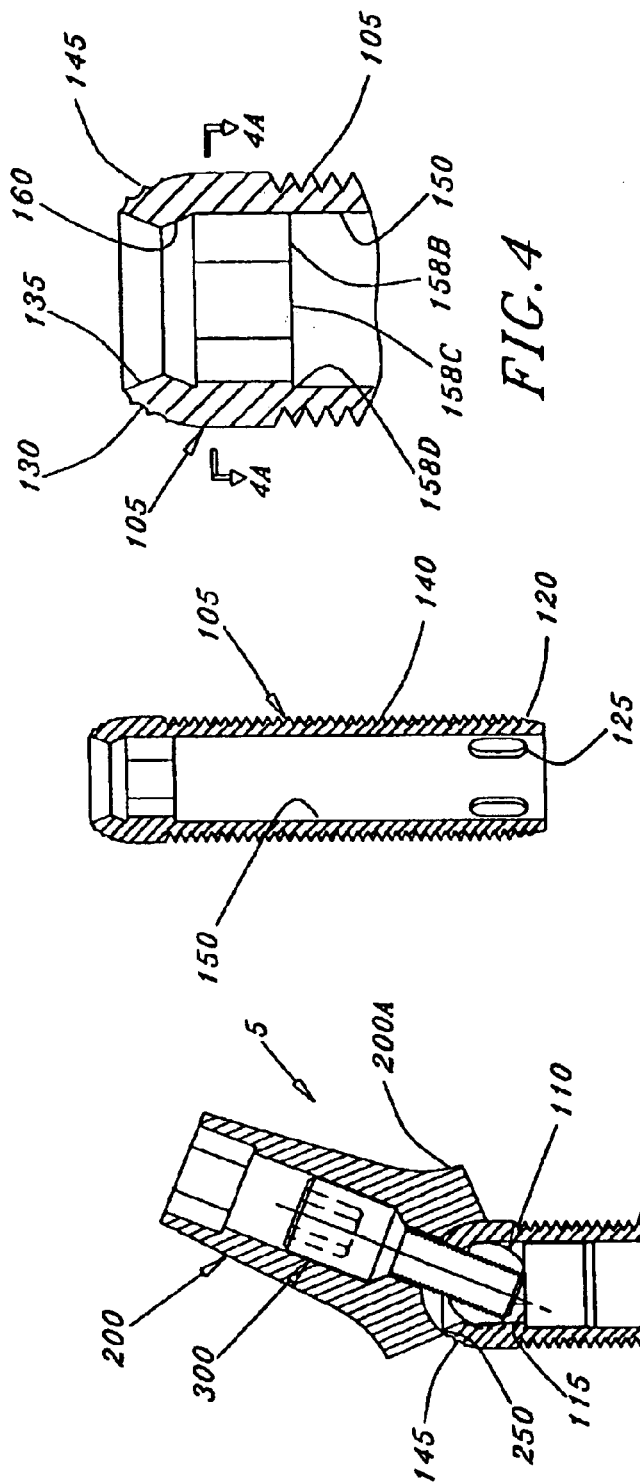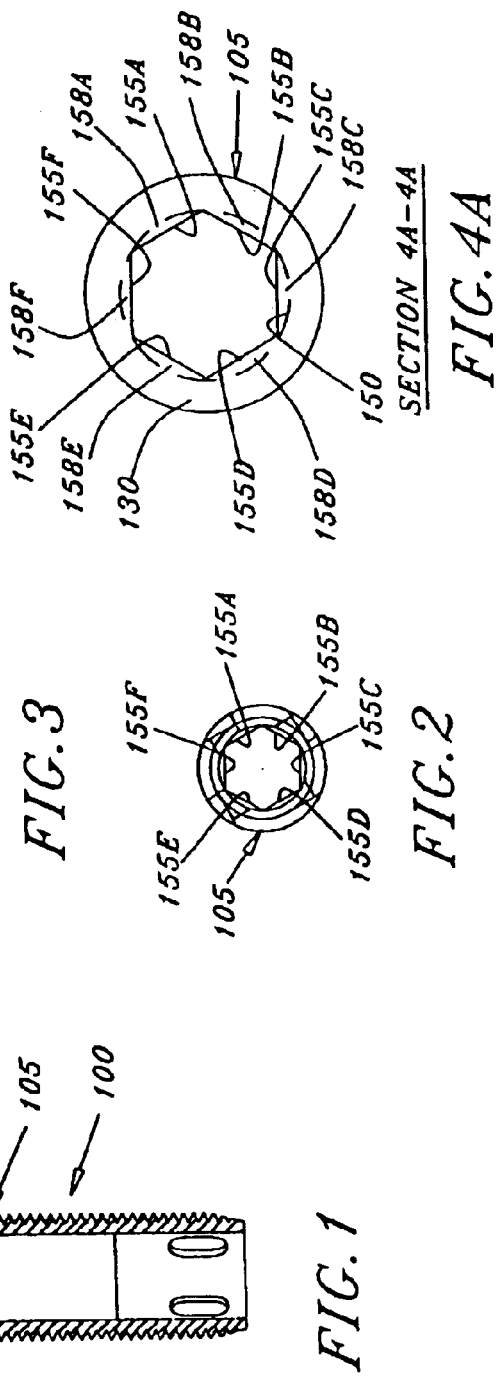

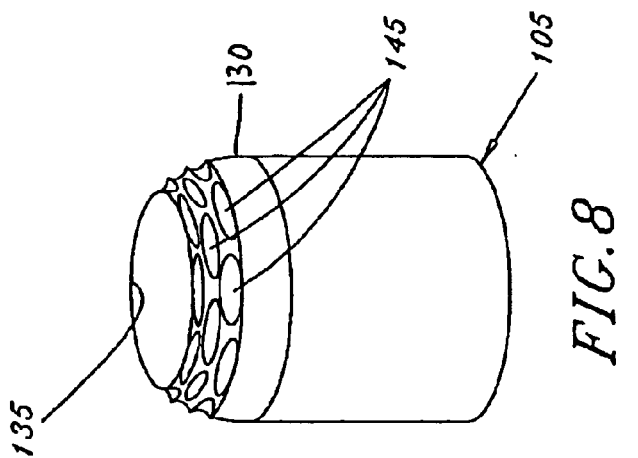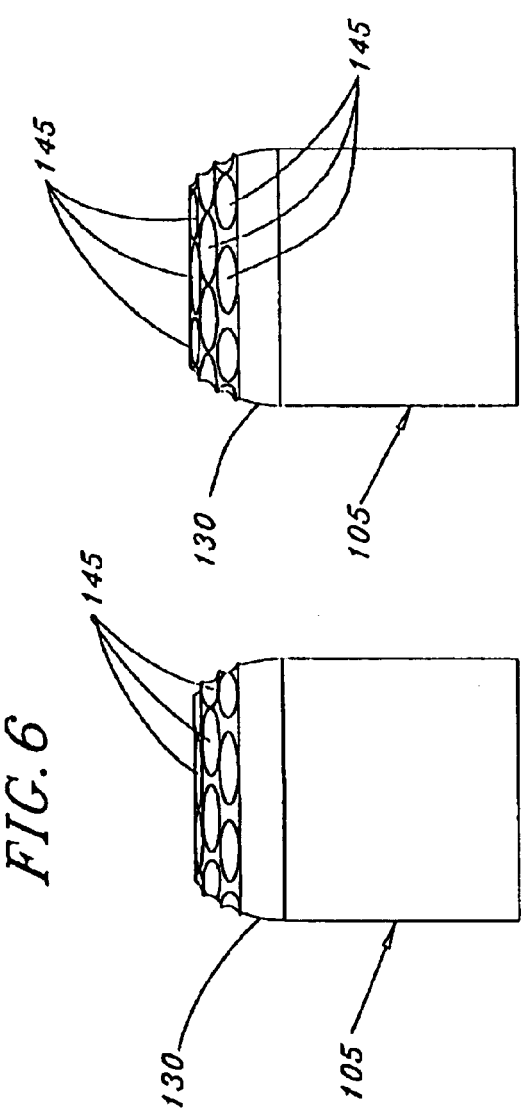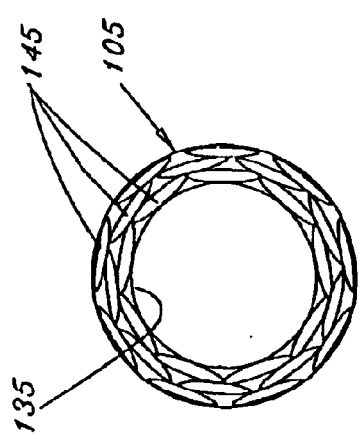

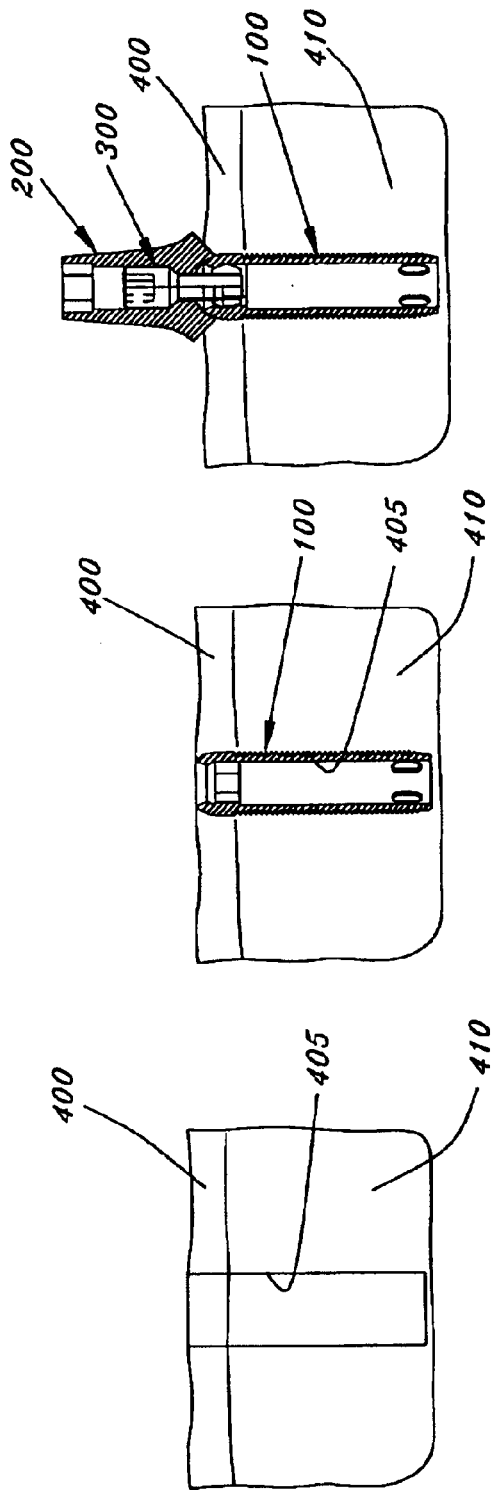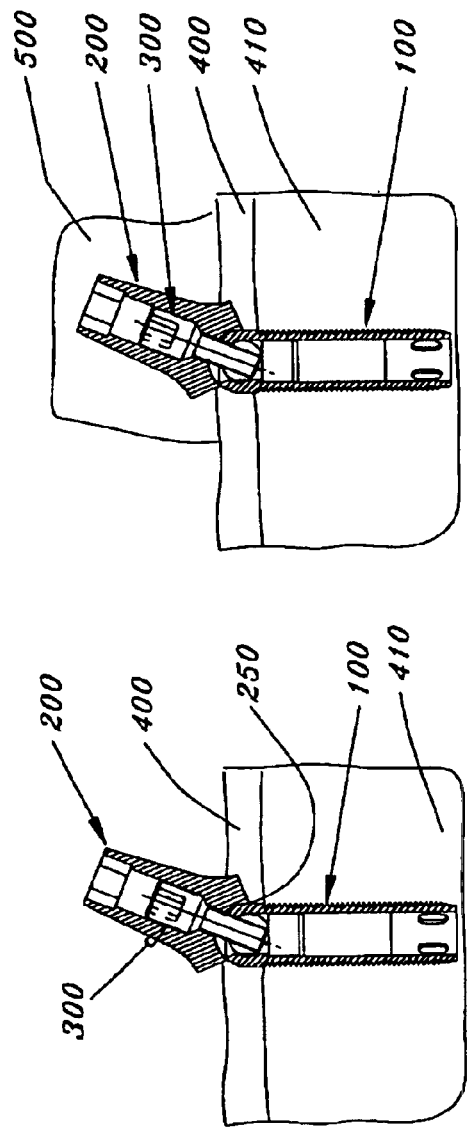
FIG. 20
FIG. 21
FIG. 22
FIG. 23
FIG. 24

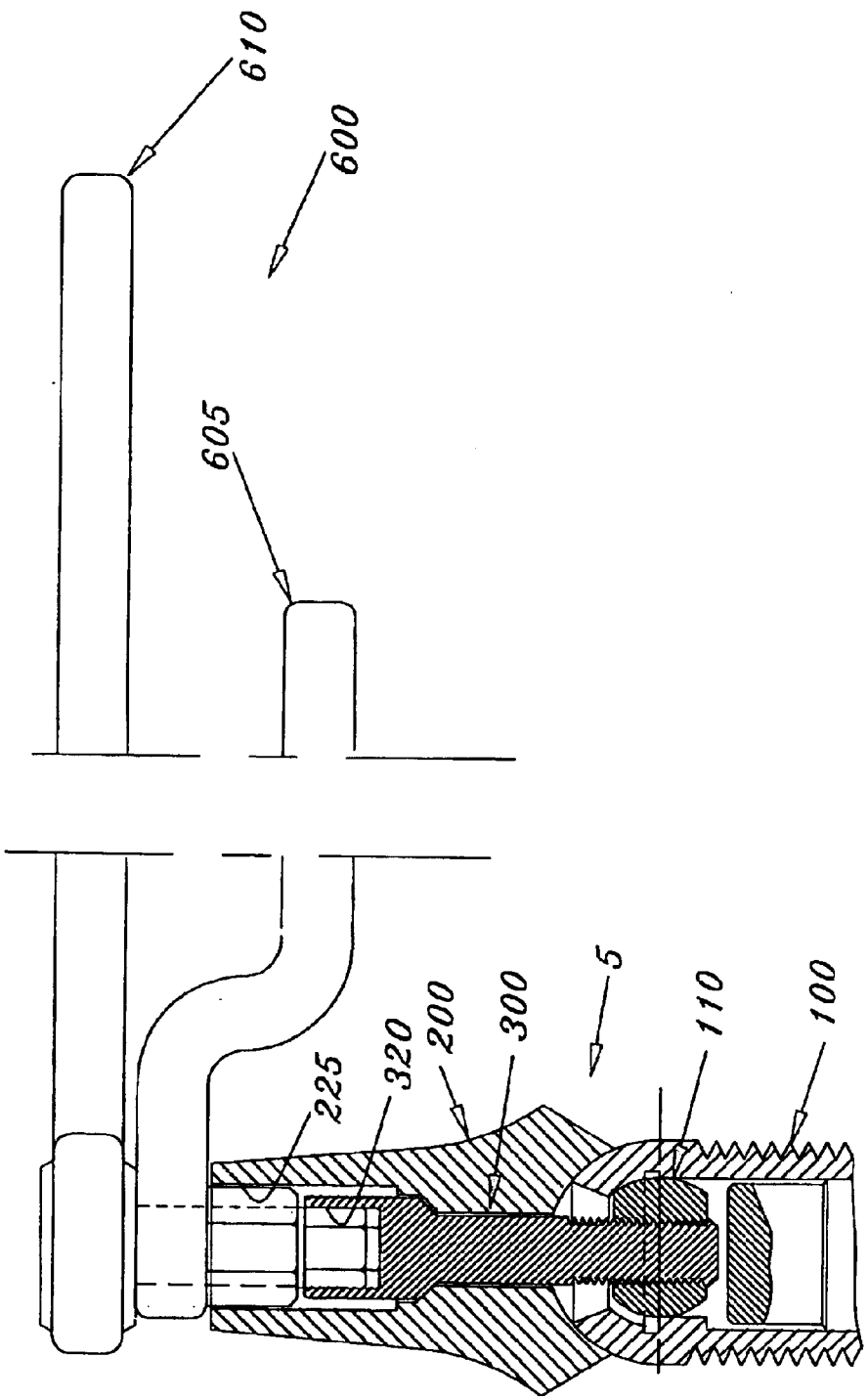

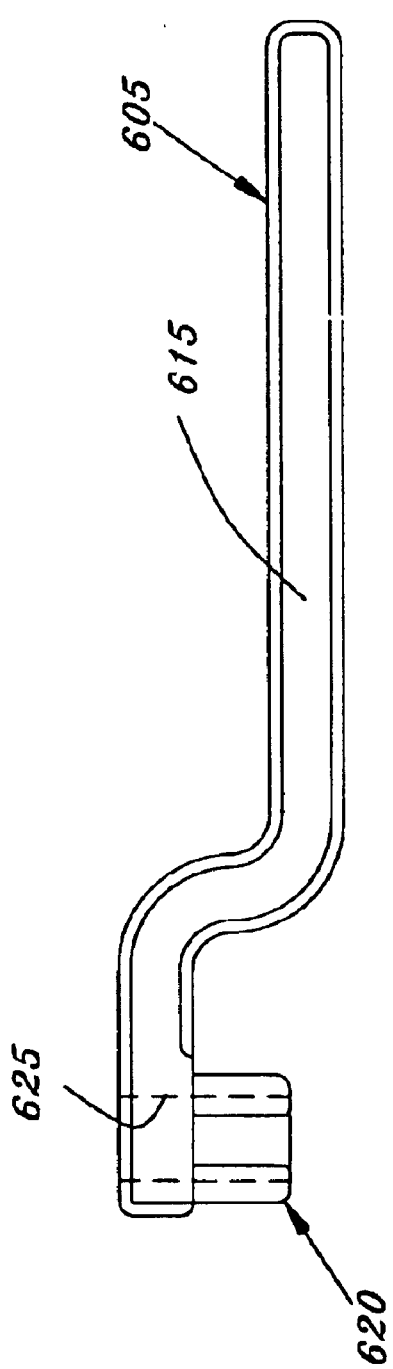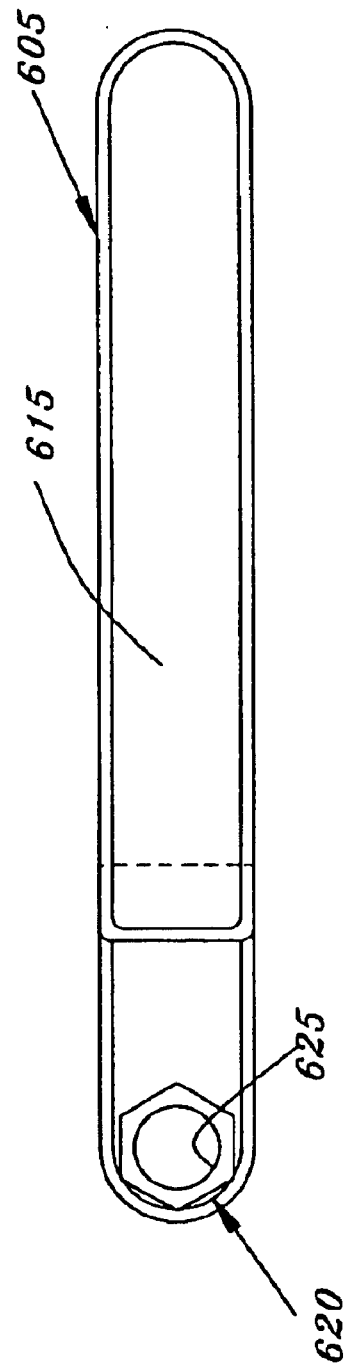

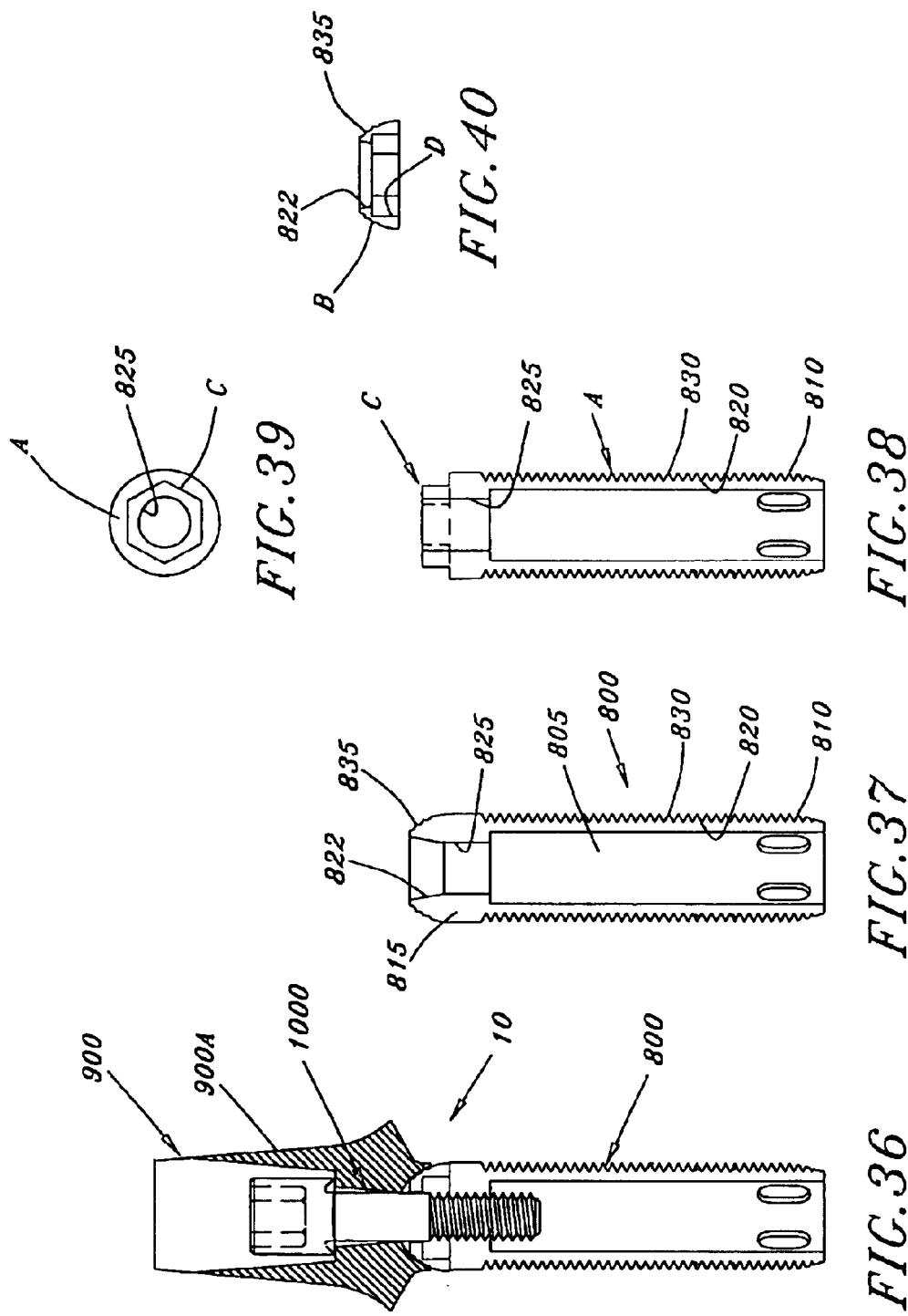

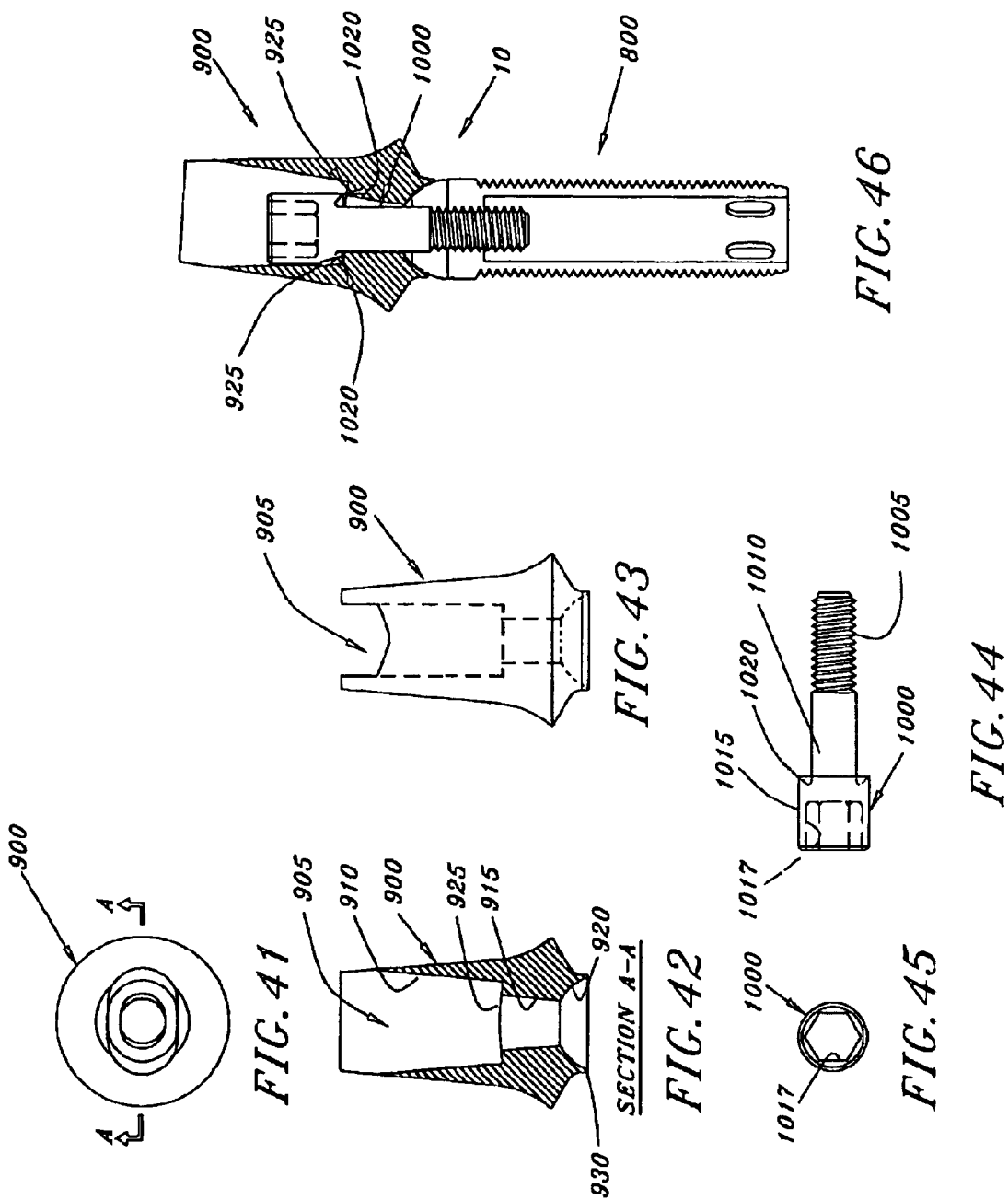

SECTION B-B

DENTAL IMPLANT AND TOOL AND METHOD FOR EFFECTING A DENTAL RESTORATION USING THE SAME

REFERENCE TO PENDING PRIOR PATENT APPLICATION

This is a continuation of prior U.S. patent application Ser. No. 09/193,933, filed Nov. 11, 1998 now U.S. Pat. No. 6,287,115 by L. Paul Lustig, Federico Castellucci and Andrew P. Tybinkowski for DENTAL IMPLANT AND TOOL AND METHOD FOR EFFECTING A DENTAL RESTORATION USING THE SAME.

FIELD OF THE INVENTION

This invention relates to dental apparatus and procedures in general, and more particularly to dental implants and tools and methods for effecting dental restorations using the same.

BACKGROUND OF THE INVENTION

In many individuals, disease and/or injury may result in the loss of one or more natural teeth. As a result, various techniques have been developed to replace such lost natural teeth with prosthetic appliances.

For example, where sufficient natural teeth remain adjacent to the location where a prosthetic tooth is to be positioned, a bridge may be fabricated.

Alternatively, if insufficient natural teeth remain to support and stabilize a bridge, a denture may be fabricated, with the denture seating against the patient's gingiva.

In still other situations, a dental implant may be used. With such a dental implant, a hole is generally first made in the upper or lower jaw bone, as appropriate, and then the distal end of the implant is fixed in the recipient bone, e.g., by screwing the implant into the bone. The dental implant is generally sized and positioned so that the proximal end of the implant protrudes at least partially into the space where the prosthetic tooth is to be positioned. Then the prosthetic tooth is fixed to the proximal end of the implant, such that the prosthetic tooth generally occupies the space of the lost tooth.

While such dental implants can be effective, they also tend to suffer from a number of problems. Among other things, with current dental implants, the longitudinal axis of the prosthetic tooth must generally follow the longitudinal axis of the implant which is seated in the bone. Unfortunately, the optimal axial alignment for the implant seated in the bone may not necessarily be the same as the optimal axial alignment for the prosthetic tooth extending into the mouth. In particular, it has been found that the optimal axial alignment for the implant tends to be dictated by the specific anatomy of the patient's recipient jaw bone, while the optimal axial alignment of the prosthetic tooth tends to be dictated by the geometry of the patient's bite, lip support, phonetics and aesthetics. Thus, with current dental implants, the dental practitioner typically faces a choice of optimizing the orientation of the restoration for either (1) the implant seated in the bone, or (2) the prosthetic tooth extending into the mouth, or (3) some compromise in between. In any case, the result is generally a compromise of some sort.

OBJECTS OF THE INVENTION

Accordingly, one object of the present invention is to provide a novel dental implant which avoids the problems associated with the prior art.

Another object of the present invention is to provide a novel tool for use in deploying the novel dental implant of the present invention.

And another object of the present invention is to provide a novel method for effecting a dental restoration.

SUMMARY OF THE INVENTION

These and other objects are addressed by the present invention, which comprises a novel dental implant, a novel tool for deploying the same, and a novel method for effecting a dental restoration.

The novel dental implant comprises an implant fixture assembly adapted for attachment to a jaw bone at a first end thereof, the implant fixture assembly having a longitudinal axis; an abutment for mounting on a second end of the implant fixture assembly, the abutment having a longitudinal axis; and a fastener for connecting the abutment to the second end of the implant fixture assembly such that the abutment is adjustably movable on the second end of the implant fixture assembly and, upon disposition of the abutment axis at a selected angle to the implant fixture assembly axis, for fixedly connecting the abutment to the second end of the implant fixture assembly such that the abutment is fixed on the implant fixture assembly at the selected angle.

In one form of the invention, a novel tool is provided for setting the abutment on the second end of the implant fixture assembly by way of a screw interconnecting the abutment and the implant fixture assembly, the tool comprising a first elongated handle having a first hole therethrough; a first driver fixed proximate a distal end of the first handle, the first driver having a hole extending centrally therethrough and in alignment with the first handle hole; a second elongated handle; a second driver fixed proximate a distal end of the second handle and extendible through the first handle hole and the first driver hole and distally beyond the first driver; the first driver being engageable with an interior portion of the abutment and the second driver being engageable with an interior portion of a head portion of the screw.

In another form of the invention, a novel tool is provided for setting the abutment on the second end of the implant fixture assembly, the implant fixture assembly being fixed at the first end thereof in a jaw bone, and the abutment being adapted to receive and retain a prosthetic tooth, the abutment having an axial cavity therein and extending therethrough, and the implant fixture assembly having a recess in the second end thereof in communication with a threaded bore in the implant fixture assembly, the abutment's axial cavity being shaped to receive the head portion of a screw and a first shank portion of that screw, and the implant fixture assembly being adapted to receive a second shank portion of the screw, the tool comprising a first elongated handle and a driver fixed on an end of the first handle, the driver and the first handle having a hole extending therethrough centrally of the driver, the driver being engageable with the abutment's axial cavity so as to hold the abutment in a nonrotative manner, and a second elongated handle and a second driver fixed on an end of the second handle, the second driver being extendible in the hole through the first handle and through the first driver so as to engage an internal recess in the head portion of the screw, wherein movement of the two handles together serves to tilt the abutment on the implant fixture assembly to a desired position, and holding the first handle stationary while rotating the second handle serves to advance the screw in the implant fixture assembly so as to lock the abutment in the desired position on the implant fixture assembly.

The novel method for effecting a dental restoration comprises the steps of attaching an implant fixture assembly to a jaw bone; attaching an abutment to the implant fixture assembly by a retaining screw so as to permit tilting movement of the abutment on the implant fixture assembly; tilting the abutment on the implant fixture assembly so as to place a longitudinal axis of the abutment at a selected angle relative to a longitudinal axis of the implant fixture assembly; and fixing the abutment on the implant fixture assembly at the selected angle.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein:

FIG. 1 is a side view in elevation of one form of dental implant formed in accordance with the present invention;

FIGS. 2–8 show various aspects of the implant fixture assembly shown in FIG. 1;

FIGS. 20–24 are side elevational views showing various steps in effecting a dental restoration using the dental implant shown in FIG. 1;

FIGS. 25–29 are various views illustrating a tool which may be used to set the abutment shown in FIG. 1;

FIG. 36 is a side view in elevation of an alternative form of a dental implant formed in accordance with the present invention;

FIGS. 37–40 show various aspects of the implant fixture assembly shown in FIG. 36;

FIGS. 41–43 show various aspects of the abutment shown in FIG. 36;

FIGS. 44 and 45 show various aspects of the fixation screw shown in FIG. 36; and FIG. 46 illustrates a different disposition of the dental implant shown in FIG. 36.

DETAILED DESCRIPTION OF THE PREFERRED EMBODIMENTS

Looking first at FIG. 1, there is shown a dental implant 5 formed in accordance with the present invention. Dental implant 5 generally comprises an implant fixture assembly 100 and an abutment 200.

Figure 12:
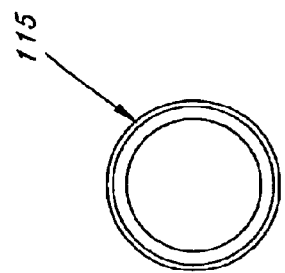
FIGS. 11 and 12 show various aspects of the plug shown in FIG. 1.
Figure 11:
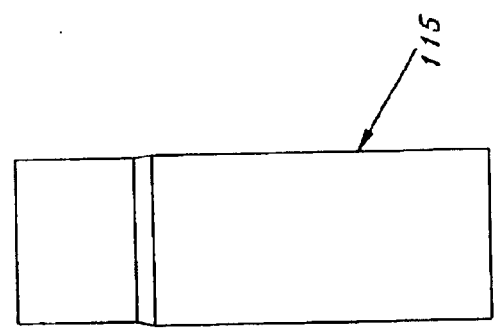

Implant fixture assembly 100 is adapted to be mounted to the patient's jaw bone. Implant fixture assembly 100 generally comprises a housing 105 (FIGS. 1–8), a floating nut 110 (FIGS. 1, 9, 10, 25, 32 and 35) and a plug 115 (FIGS. 1, 11 and 12).

Housing 105 (FIGS. 1–8) comprises a hollow, sleeve-like structure having a distal end 120 (FIG. 3) terminating in an opening 125 (FIG. 3), and a proximal end 130 (FIGS. 4, 5, 7, 8, 32 and 35) terminating in an opening 135 (FIGS. 4, 6, 8 and 32). Screw threads 140 (FIG. 3) are formed on the outer surface of housing 105 and extend from distal end 120 toward proximal end 130, stopping just short of proximal end 130 (see FIG. 4).

Proximal end 130 comprises a generally semi-spherical geometry (FIGS. 4, 5, 7, 8, 32 and 35), and includes a plurality of sharp facets 145 (FIGS. 1, 4 and 5–8) formed thereon. Facets 145 are preferably formed on the housing's proximal end 130 so as to form a concentric pattern about the housing's semi-spherical dome (FIGS. 5–8). However, facets 145 may also be formed on the housing's proximal end 130 in other configuration as well, e.g., they may be disposed in a matrix-like configuration, or some other ordered pattern (such as the concentric ribs 145A shown in FIGS. 6A and 8A), or they may be disposed in a substantially random pattern (for example, by roughening the outer surface of housing proximal end 130). In any case, facets 145 are created so as to form relatively sharp, substantially clearly-delineated surfaces extending about the generally semi-spherical surface of the housing's proximal end 130 for engagement with circular rim 250 of abutment 200 as discussed in further detail below.

The interior of housing 105 is formed so that a passageway 150 (FIGS. 1, 3, 4 and 4A) of constant diameter extends from distal opening 125 toward proximal end 130. At the proximal end 130 of housing 105, the housing defines a substantially hexagonal chamber 155 (FIG. 4), which hexagonal chamber is defined by six planar surfaces 155A, 155B, 155C, 155D, 155E and 155F (FIGS. 2 and 4A). Preferably hexagonal chamber 155 is sized so that its six corner apexes are aligned with the wall of passageway 150, and so that its three pairs of opposing surfaces (i.e., surfaces 155A and 155D, surfaces 155B and 155E, and surfaces 155C and 155F) have a narrower diameter than passageway 150, as seen in FIG. 4A. In this way, six lands or stops 158A, 158B, 158C, 158D, 158E and 158F are formed at the intersection of passageway 150 and hexagonal chamber 155 (FIGS. 4 and 4A). At the proximal end of hexagonal chamber 155, housing 105 is undercut so as to form an inclined surface 160 (FIG. 4) which narrows hexagonal chamber 155 to the size of proximal opening 135. Surface 160 can be planar or arcuate when viewed in cross-section, as desired.

Thus it will be seen that hexagonal chamber 155 and inclined surface 160 connect the housing's interior passageway 150 with proximal opening 135 (FIG. 4). It is to be appreciated that the housing's central lumen narrows as it passes from interior passageway 150 to proximal opening 135, due to the fact that the six surfaces 155A–155F (making up hexagonal chamber 150) have a generally smaller diameter than central passageway 150, and due to the fact that surface 160 is inclined proximally and distally in the manner shown in FIG. 4.

Figure 10:
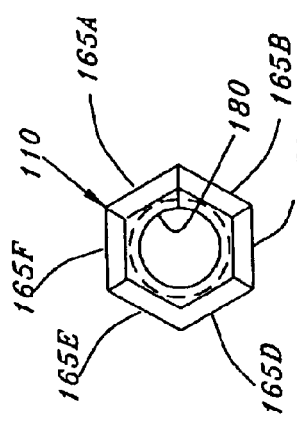
FIGS. 9 and 10 show various aspects of the floating nut shown in FIG. 1.
Figure 9:
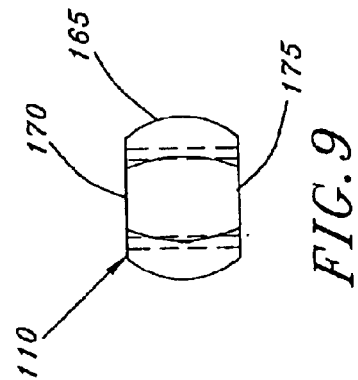

Floating nut 110 (FIGS. 1, 9, 10, 25, 32 and 35) comprises a substantially hexagonal outer wall 165 (FIG. 9) made up of six semi-spherical surfaces 165A, 165B, 165C, 165D, 165E and 165F (FIG. 10). Floating nut 110 terminates in a pair of end surfaces 170, 175 (FIG. 9). A threaded bore 180 (FIG. 10) extends through floating nut 110, from end surface 170 to end surface 175. Floating nut 110 is sized and shaped so that its six semi-spherical surfaces 165A–165F will make a close sliding fit with the housing's six planar surfaces 155A–155F when floating nut 110 is disposed in hexagonal chamber 155 (FIG. 1), as will hereinafter be discussed.

Plug 115 (FIGS. 1, 11 and 12) comprises a generally cylindrical structure. Plug 115 is sized so that it can be press fit within interior passageway 150 (FIG. 1) of housing 105.

Implant fixture assembly 100 is intended to be assembled by first loading floating nut 110 into the open distal end 125 (FIG. 3) of housing 105, with the floating nut's threaded bore 180 being generally axially aligned with the longitudinal axis of housing 105, and then moving floating nut 110 down housing 105 until the nut is located within hexagonal chamber 155, with the nut's semi-spherical surfaces 165A–165F (FIGS. 9 and 10) slidingly engaging the six planar surfaces 155A–155F of hexagonal chamber 155 (FIGS. 2 and 4). Then plug 115 is press fit into the distal end 125 of housing 105 and advanced proximally until the proximal end of plug 115 engages stops 158A–158F located at the distal end of hexagonal chamber 155 (FIG. 1). In this way, floating nut 110 is movably captured in hexagonal chamber 155, between the housing's inclined surface 160 and the proximal end of plug 115.

It is to be appreciated that when floating nut 110 is movably captured in this position, the nut's threaded bore 180 will communicate with the opening 135 (FIG. 4) formed in proximal end 130 of housing 105, whereby the nut's threaded bore 180 can be engaged by an appropriate screw extending into the open proximal end of housing 105, as will hereinafter be discussed.

It is also to be appreciated that, due to the corresponding geometries of hexagonal chamber 155 and nut wall 165, floating nut 110 can pivot in hexagonal chamber 155 about the longitudinal axis of the nut's threaded bore 180 (i.e., clockwise and counterclockwise, as viewed in FIG. 9; see also FIGS. 15–17), but will be held against rotation about the same axis (i.e., it will be held against rotation in a clockwise and counterclockwise sense, as viewed in FIG. 10). As a result of this construction, floating nut 110 will be able to receive the nose of a screw set at a variety of different axial alignments relative to housing 105, but will be held against rotation as that screw is screwed into and out of the floating nut.

Figure 17:
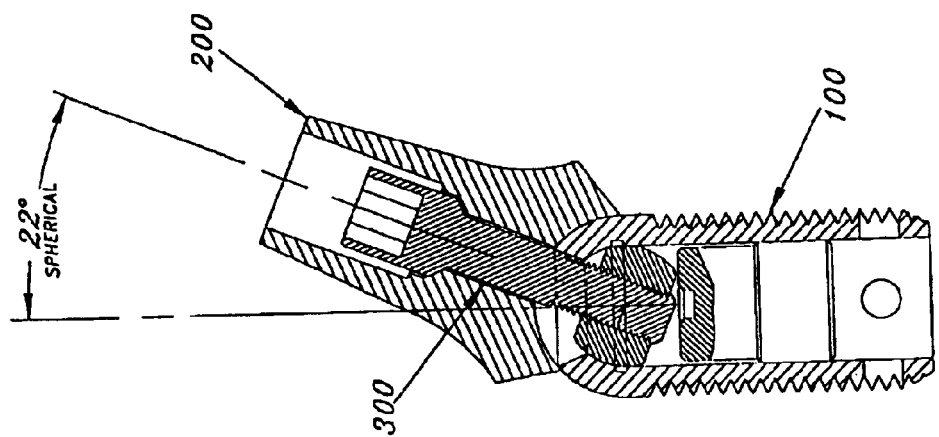
FIGS. 15–17 show different dispositions of the dental implant shown in FIG. 1.
Figure 16:
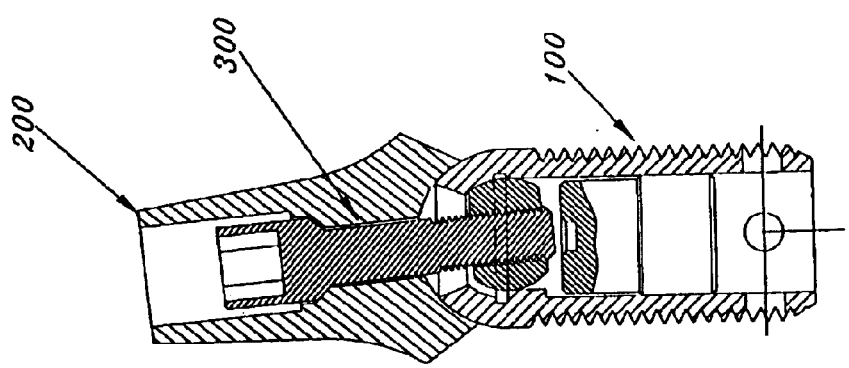
Figure 15:
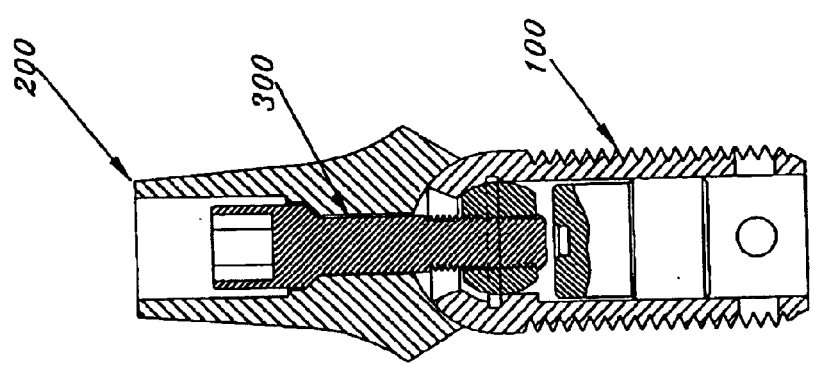

It should be appreciated that it is important to set the degree of pivot permitted floating nut 110 about the longitudinal axis of its threaded bore 180 (i.e., clockwise and counterclockwise, as viewed in FIG. 9; see also FIGS. 15–17). On the one hand, if floating nut 110 is permitted to pivot too far about this axis, its threaded bore 180 may not be easily accessible through the housing's proximal opening 135. On the other hand, if floating nut 110 is not permitted to pivot far enough about this axis, it may unduly limit the axial alignment of abutment 200, as will hereinafter be made clear. In the present design, the degree of pivot permitted floating nut 110 in hexagonal chamber 155 is established by the engagement of the floating nut's end surface 175 with the proximal end of plug 115; and this point of engagement is in turn determined by the position of the proximal end of plug 115 within housing 105. As noted above, plug 115 is positioned so that its proximal end contacts stops 158A–158F.

Figure 13:
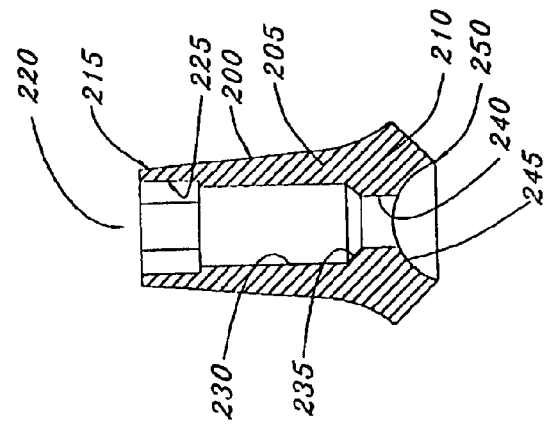

Abutment 200 (FIGS. 1, 13–17 and 22–25) comprises a body 205 (FIG. 13) having a distal end 210 and a proximal end 215. A multi-stage bore 220 extends axially through abutment 200, from proximal end 215 to distal end 210. Multi-stage bore 220 comprise a first, hexagonally-shaped portion 225; second, cylindrically-shaped portion 230; a third, frustoconically-shaped portion 235; a fourth, cylindrically-shaped portion 240; and a fifth, hemispherically-shaped portion 245. The portion of body 205 located adjacent to fifth, hemispherically-shaped bore portion 245 defines a relatively sharp, circular end rim 250 (FIG. 13).

Figure 6A:
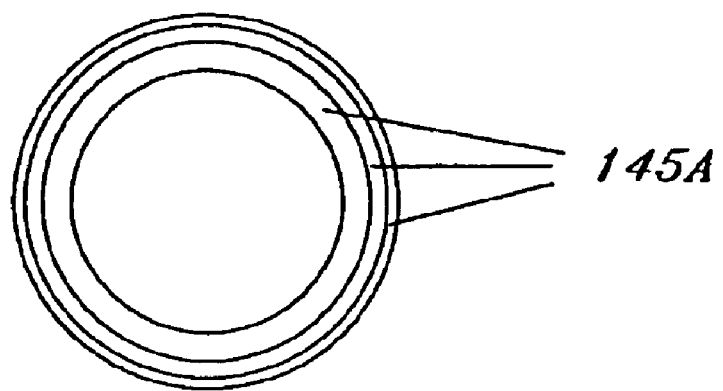
Figure 8A:
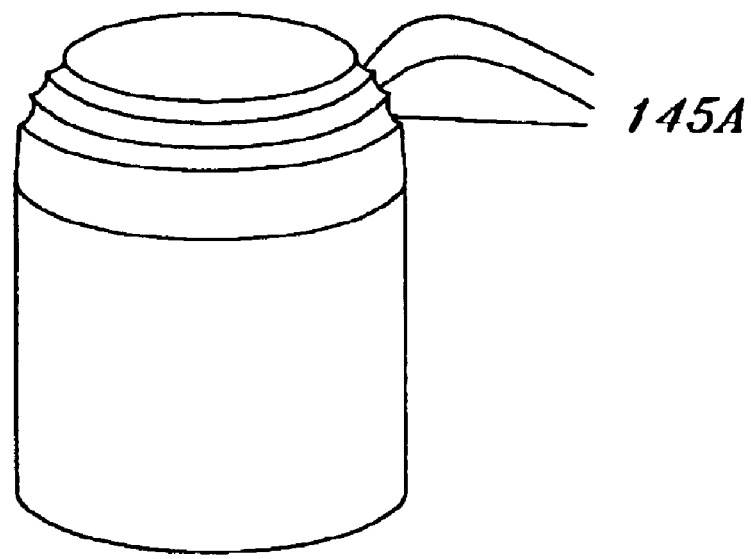
Figure 14:
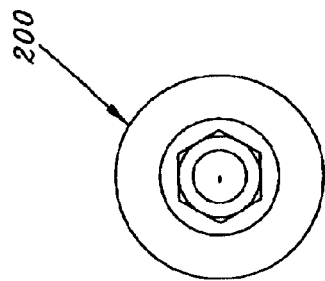
FIGS. 13 and 14 show various aspects of the abutment shown in FIG. 1.

Abutment 200 is sized so that its distal end 210 can fit over proximal end 130 of implant fixture assembly 100 (FIG. 1), with the abutment's hemispherically-shaped bore portion 245 mating with the correspondingly-shaped proximal end 130 of implant fixture assembly 100, and with the abutment's circular rim 250 engaging selected ones of facets 145 (FIGS. 1, 4 and 6–8) or facets 145A (FIGS. 6A and 8A). It will be appreciated that, due to the semi-spherical nature of the surfaces involved, implant fixture assembly 100 and abutment 200 can mate solidly with each other in a wide variety of different axial angles (see, for example, FIGS. 1 and 15–17).

Figure 19:
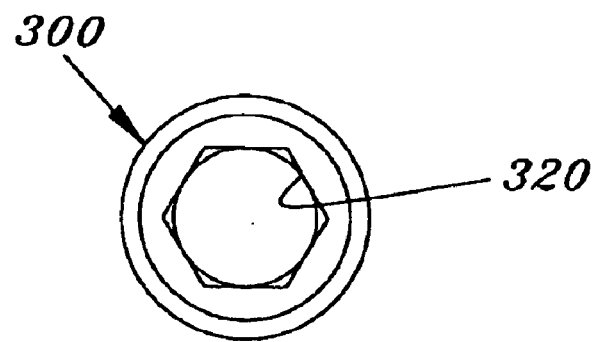
FIGS. 18 and 19 show various aspects of the fixation screw shown in FIG. 1.
Figure 18:
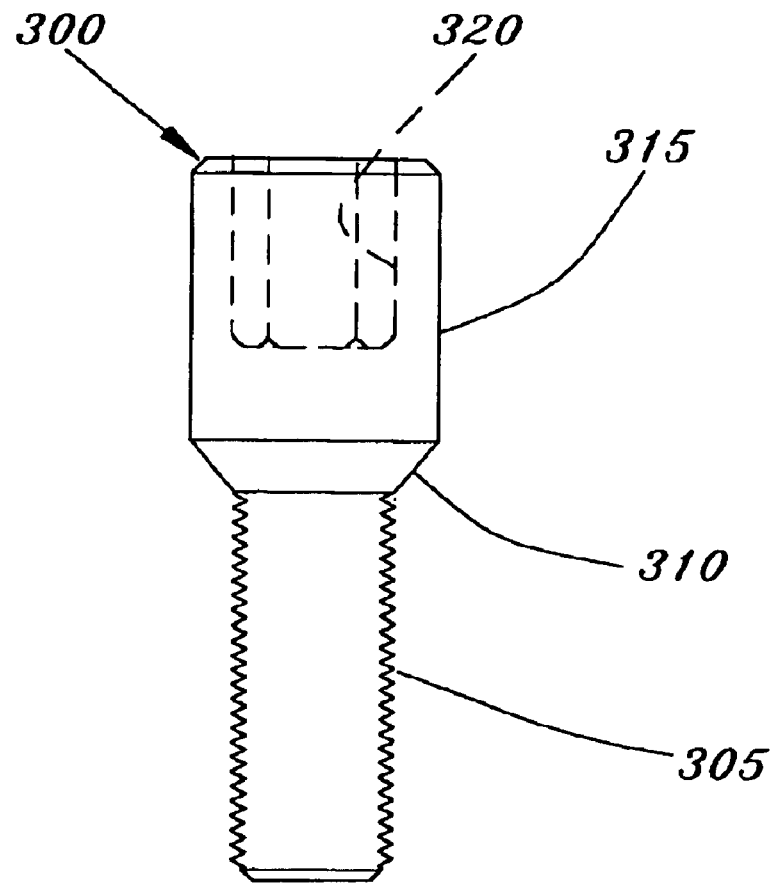

A fixation screw 300 (FIGS. 1, 18, 19, 22, 23, 24 and 25) is used to attach abutment 200 to implant fixture assembly 100. Fixation screw 300 generally comprises a threaded distal portion 305 (FIG. 18), a frustoconical intermediate portion 310, and a cylindrical proximal portion 315. Threaded distal portion 305 is sized so that it can pass through the abutment's multi-stage bore 220 (FIG. 13) and threadedly engage threaded bore 180 of floating nut 110 (FIGS. 1 and 15–17). At the same time, the fixation screw's frustoconical intermediate portion 310 is sized and shaped so that it will mate with the third, frustoconically shaped portion 235 (FIG. 13) of the abutment's multi-stage bore 220 (FIGS. 1 and 15–17). In addition, the screw's cylindrical proximal portion 315 (FIG. 18) is sized so that it will slidingly fit within the second, cylindrically-shaped portion 230 (FIG. 13) of the abutment's multi-stage bore 220. A hexagonally-shaped recess 320 (FIGS. 18, 19 and 25) is formed in the fixation screw's cylindrical proximal portion 315, whereby the fixation screw may be rotated, e.g., by a driver.

Dental implant 5 is intended to be used as follows.

First, an opening is formed in the patient's gingiva 400 (FIG. 20), and then a hole 405 is formed in the patient's jaw bone 410 (FIG. 20). In accordance with the present invention, hole 405 is formed so as to substantially optimize the safe and secure attachment of implant fixture assembly 100 to jaw bone 410. Then implant fixture assembly 100, previously assembled, is screwed, distal end first, into jaw bone 410 (FIG. 21). As this is done, it is preferred, for the sake of subsequent convenience, that floating nut 110 be oriented within housing 105 so that the nut's threaded bore 180 is substantially aligned with the longitudinal axis of the housing, in the manner shown in FIG. 21. This disposition ensures that the nut's threaded bore 180 may thereafter be easily accessed through the housing's proximal opening 135 (FIG. 4).

Next, distal end 210 (FIG. 13) of abutment 200 is brought into engagement with the proximal end 130 (FIG. 4) of implant fixture assembly 100, and fixation screw 300 is used to loosely secure the two members together (FIG. 22). More particularly, fixation screw 300 is initially only loosely screwed into floating nut 110 of implant fixture assembly 100, such that abutment 200 will be held to implant fixture assembly 100, yet still be capable of being moved about relative to implant fixture assembly 100. The dental practitioner then selects the precise orientation desired for abutment 200 relative to implant fixture assembly 100. In accordance with the present invention, abutment 200 is intended to be oriented so as to substantially optimize the orientation of a prosthetic tooth which will subsequently be attached to the proximal end 215 (FIG. 13) of abutment 200.

Once the proper orientation of abutment 200 has been established, fixation screw 300 is tightened (or torqued) with the proper torque all the way down (FIG. 23), whereupon end rim 250 (FIGS. 1 and 13) of abutment 200 will securely engage selected ones of the housing's facets 145 or 145A, whereby subsequent slippage of abutment 200 relative to implant fixture assembly 100 will be prevented. If it is thereafter determined that the alignment of abutment 200 needs to be adjusted, fixation screw 300 may be loosened and the process repeated.

Thereafter, after the deployment of dental implant 5 has been finalized, a prosthetic tooth 500 (FIG. 24) may be fabricated in ways well known in the art, and then attached onto abutment 200, also in ways well known in the art. By way of example but not limitation, once the deployment of dental implant 5 has been finalized, an impression of the patient's mouth may then be made, this impression thereafter used to fabricate prosthetic tooth 500, and then the prosthetic tooth cemented onto abutment 200. It should also be appreciated that the cement used to hold the prosthetic tooth onto abutment 200 will fill the multistage bore 220 and help hold fixation screw 300 fast.

It is to be appreciated that with the dental implant 5 described above, fixation screw 300 follows the orientation of the abutment's multi-stage bore 220 (FIGS. 1 and 13) and not (necessarily) the orientation of housing 105, as seen in FIGS. 23 and 24.

Figure 29:
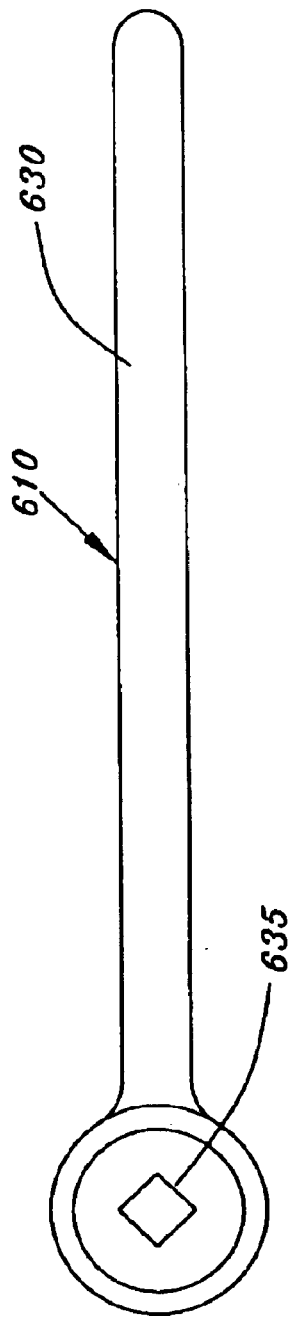
Figure 28:
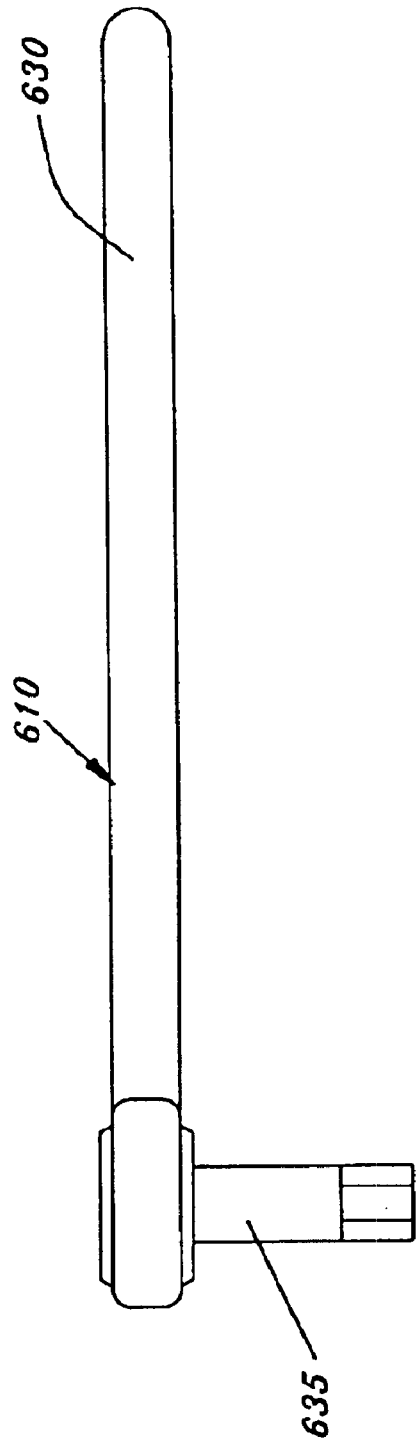

If desired, a tool 600 (FIGS. 25–29) may be conveniently used to attach abutment 200 to implant fixture assembly 100. Tool 600 generally comprises a first element 605 (FIGS. 25–27) and a second element 610 (FIGS. 25, 28 and 29). Second element 610 preferably comprises a torque wrench. First element 605 (FIGS. 25–27) includes a handle 615 and a working end 620. Working end 620 essentially comprises a driver mounted to the end of handle 615. A bore 625 extends through handle 615 and working end 620. Working end 620 is sized and shaped so as to fit within, and securely engage, the first hexagonally-shaped portion 225 (FIG. 13) of the multi-stage bore 220 formed in abutment 200. Second element 610 (FIGS. 25, 28 and 29) includes a handle 630 and a working end 635. Working end 635 essentially comprises an elongated second driver mounted to the end of handle 630. Working end 635 is sized so as to pass through bore 625 formed in first element 605 and then fit within, and drivingly engage, the hexagonally-shaped recess 320 (FIGS. 18 and 19) of fixation screw 300. As a result of this construction, the tool's first element 605 permits abutment 200 to be held against rotation (FIG. 25) while the tool's second element 610 permits fixation screw 300 to be turned down into, or withdrawn from, engagement with floating nut 110. By fabricating second element 610 in the form of a torque wrench, the dental practitioner is quickly and easily able to set fixation screw 300 with the desired amount of torque.

It should be appreciated that, by virtue of the fact that abutment 200 is held against rotation while fixation screw 300 is turned down into, or withdrawn from, engagement with floating nut 110, high torque forces are not applied directly to implant fixture assembly 100. As a result, abutment 200 may be tightened to implant fixture assembly 100 with the highest possible torque forces, without fear of undermining the osseo-integration of implant fixture assembly 100 to bone 410.

It should also be appreciated that, inasmuch as tool 600 comprises two interoperative elements 605 and 610, with element 605 engaging abutment 200 and element 610 engaging fixation screw 300, movement of the two elements 605 and 610 together can be used to tilt abutment 200 on implant fixture assembly 100 to the desired position, and movement of second element 610 relative to first element 605 can be used to move fixation screw 300 towards and away from floating nut 110.

In some circumstances it may be desirable to permit a period of healing to occur between placement of implant fixture assembly 100 in jaw bone 410 and the subsequent attachment of abutment 200 to implant fixture assembly 100. In this case, it is generally desirable to temporarily cap off opening 135 of implant fixture assembly 100.

Figure 31:
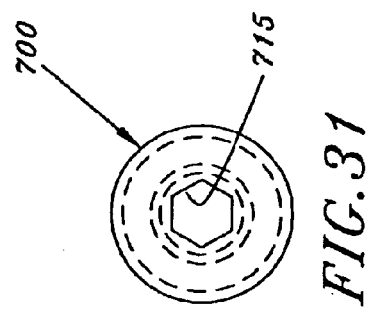
Figure 30:
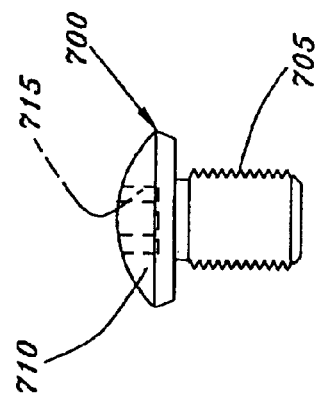

To this end, a "healing" cover screw 700 (FIGS. 30–32) is provided. Cover screw 700 comprises a threaded post 705 (FIGS. 30 and 32) for engagement with the threaded bore 180 (FIG. 10) of floating nut 110, an enlarged head 710 for seating in (and sealing off) opening 135 (FIG. 4) of implant fixture assembly 100, and a hexagonally-shaped recess 715 for receiving a wrench, by which cover screw 700 may be screwed into, or removed from, implant fixture assembly 100.

Figure 32:
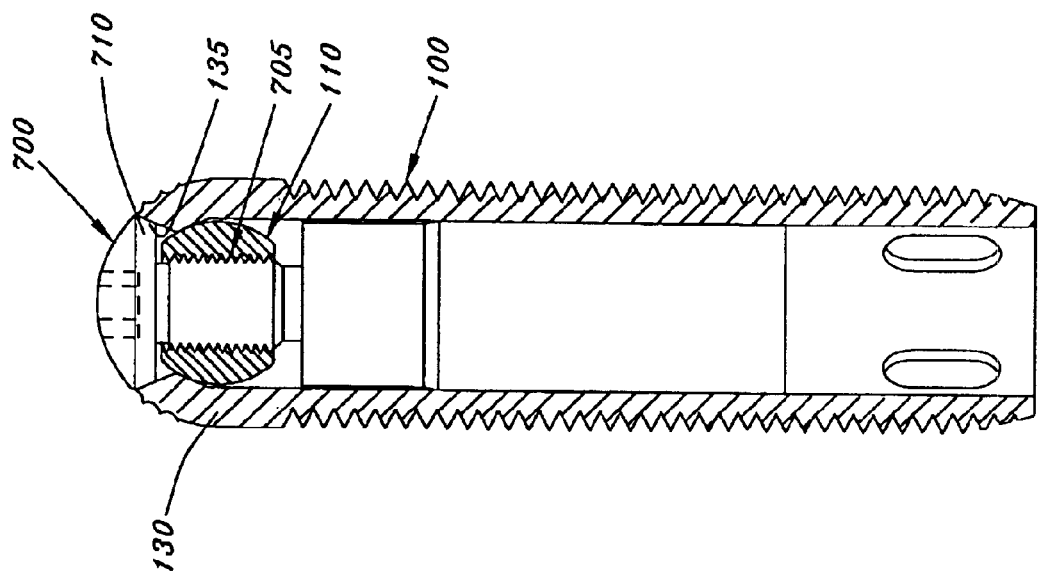
FIGS. 30–32 show various aspects of a cover screw which may be used in conjunction with the dental implant shown in FIG. 1, with FIG. 32 showing the cover screw mounted to the implant fixture assembly.

FIG. 32 shows how cover screw 700 may be screwed into opening 135 of implant fixture assembly 100 so as to close off the open proximal end of the implant fixture assembly.

In effect, cover screw 700 forms a sort of plug for closing off the opening 135 (FIGS. 4 and 32) formed in the proximal end 130 of implant fixture assembly 100 while the gingiva heals over it.

In use, implant fixture assembly 100 is deployed in bone 410 in the manner previously described, cover screw 700 is used to close off opening 135 of implant fixture assembly 100, and then gingiva 400 closed. After an appropriate period of healing, during which implant fixture assembly 100 can osseo-integrate with bone 410, gingiva 400 is re-opened, cover screw 700 is removed from implant fixture assembly 100, and then abutment 200 is attached to implant fixture assembly 100 using fixation screw 300 in the manner previously described.

Figure 35:
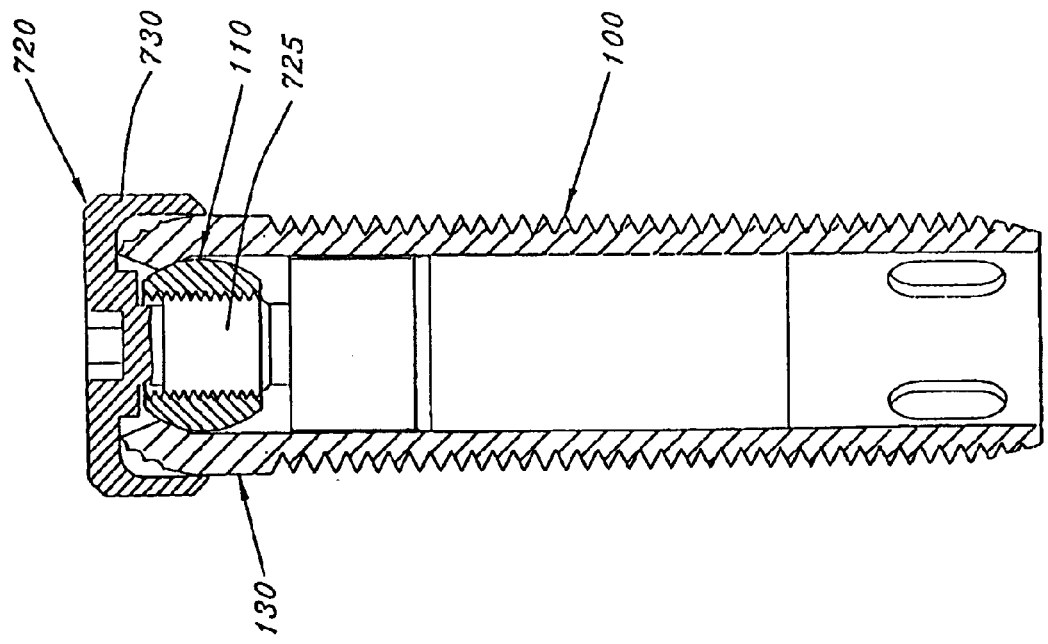
FIGS. 33–35 show various aspects of an alternative form of cover screw which may be used in conjunction with the dental implant shown in FIG. 1, with FIG. 35 showing the alternative form of cover screw mounted to the implant fixture assembly.
Figure 34:
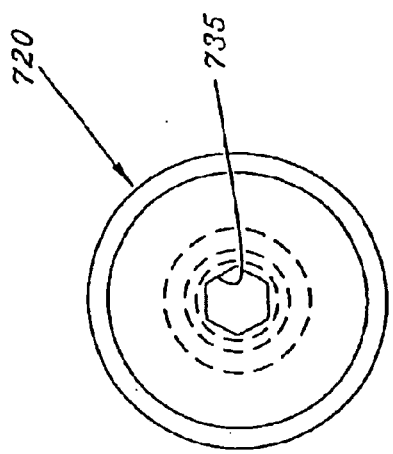
Figure 33:
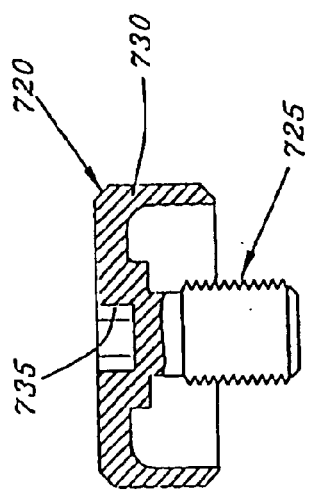

An alternative cover screw 720 (FIGS. 33–35) is also provided. Cover screw 720 comprises a threaded post 725 (FIGS. 33 and 35) for engagement with the floating nut's threaded bore 180, an enlarged head 730 for seating over (and capping off) proximal end 130 of housing 105, and a hexagonally-shaped recess 735 for receiving a wrench, by which cover screw 720 may be screwed onto, or removed from, implant fixture assembly 100. Cover screw 720 is used in substantially the same manner as the cover screw 700 previously described, except that the enlarged head 730 of cover screw 720 is adapted to cover a substantial portion of the distal end 130 of implant fixture assembly 100 (FIG. 35). In effect, cover screw 720 forms a sort of top cap for distal end 130 of implant fixture assembly 100. This can prevent bone from growing over the implant's facets.

Looking next at FIG. 36, an alternative dental implant 10 is shown. Dental implant 10 generally comprises an implant fixture assembly 800 and an abutment 900.

Figure 37A:
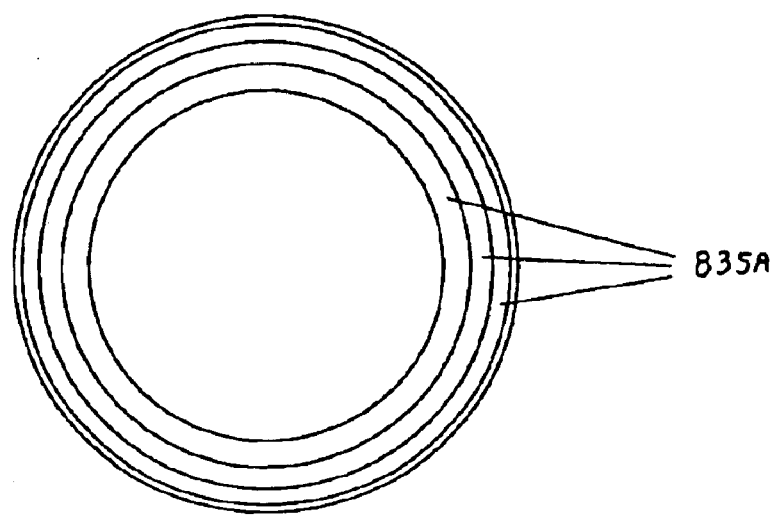
Figure 37B:
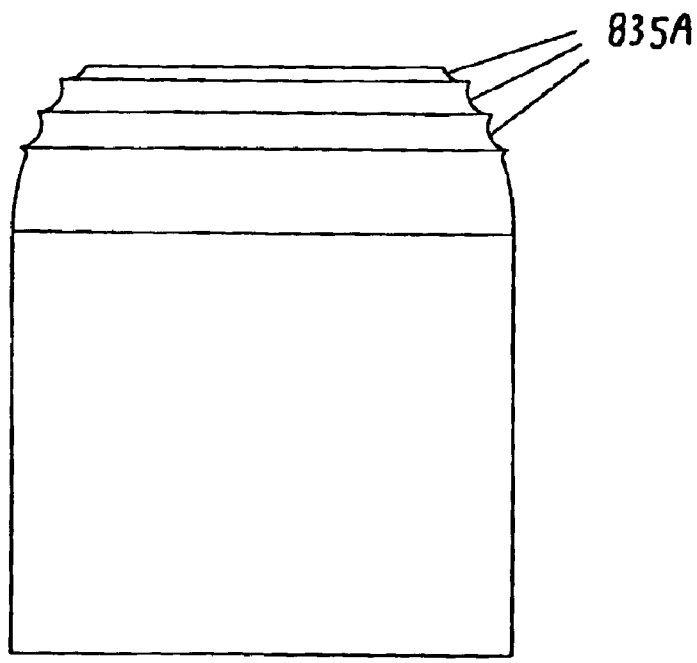

Implant fixture assembly 800 (FIGS. 36 and 37) is adapted to be mounted to the patient's jaw bone. Implant fixture assembly 800 generally comprises a housing 805 having a distal end 810 and proximal end 815. Housing 805 is preferably formed with a distal bore 820 extending proximally from distal end 810, a proximal opening 822 opening on the proximal end of the housing, and an intermediate, threaded bore 825 connecting distal bore 820 with proximal opening 822. Distal bore 820, proximal opening 822 and intermediate threaded bore 825 are all aligned with the longitudinal axis of housing 805. Screw threads 830 are formed on the outer surface of housing 805 and extend from distal end 810 toward proximal end 815, stopping just short of proximal end 815.

Proximal end 815 comprises a generally semi-spherical geometry (FIGS. 36 and 37) and includes a plurality of sharp facets 835 formed thereon. Facets 835 are preferably formed on the housing's proximal end 815 so as to form a concentric pattern about the housing's semi-spherical dome. However, facets 835 may also be formed on the housing's proximal end 815 in other configurations as well, e.g., they may be disposed in a matrix-like configuration, or some other ordered pattern (such as the concentric ribs 835A shown in FIGS. 37A and 37B), or they may be disposed in a substantially random pattern (for example, by roughening the outer surface of housing proximal end 815). In any case, facets 835 are created so as to form a plurality of relatively sharp, substantially clearly-delineated surfaces extending above the generally semi-spherical surface of the housing's proximal end 815 for engagement with annular end rim 930 of abutment 900.

If desired, implant fixture assembly 800 can be fabricated from a single piece of material.

Alternatively, implant fixture assembly 800 can be formed out of a housing A (FIGS. 38 and 39) and an adapter B (FIG. 40), with the two being joined together so as to form the complete implant fixture assembly 800. In such a case, housing A might comprise an implant element of the sort well known in the art, where the element has a hex configuration C at its proximal end for turning the element into or out of a bone with a wrench; and adapter B might comprise a counterpart hex-shaped recess D, whereby adapter B can be seated upon housing A so as to form the complete implant fixture assembly 800. Such a two-part construction can be advantageous in certain situations, such as where the patient might already have had a dental implant involving a housing A, and that housing A is already osseo-integrated into a jaw bone. In such a case, implant fixture assembly 800 can be formed in-situ, simply by mounting adapter B to the osseo-integrated housing A.

Abutment 900 (FIGS. 36 and 41–43) comprises a multi-stage passageway 905 (FIG. 42) comprising a first stage 910, a second stage 915 and a third stage 920. First stage 910 widens laterally as it approaches the distal end of abutment 900 (FIGS. 41 and 42). A shoulder 925 (FIG. 42) is formed at the intersection of first stage 910 and second stage 915. Third stage 920 is substantially identical to the fifth, hemispherically-shaped portion 245 previously described with respect to abutment 200 (FIG. 13), i.e., it has a hemispherical shape which is complimentary to the semi-spherical geometry formed at the proximal end of the implant housing. Third stage 920 terminates in a relatively sharp annular end rim 930 which is substantially identical to the annular end rim 250 (FIG. 13) described above with respect to abutment 200.

As a result of this construction, abutment 900 can be movably seated atop implant fixture assembly 800, with the abutment's hemispherically-shaped bore portion 920 riding on the implant's semi-spherically-shaped proximal end 815, and with the abutment's end rim 930 engaging selected ones of facets 835. Thus, abutment 900 can be moved about through a range of different positions atop implant fixture assembly 800 (see FIGS. 36 and 46).

It is to be understood that the first stage 910 of multi-stage passageway 905 may have any one of several shapes within the scope of the invention in its broadest aspects.

Thus, first stage 910 might be frusto-conical in shape, with its narrow end adjacent to second stage 915. This configuration will allow the longitudinal axis of the abutment to be set at a selected angle in any one of multiple planes containing the longitudinal axis of implant fixture assembly 800 in a manner analogous to that discussed above with respect to the embodiment of the invention shown in FIG. 1.

Alternatively, the first stage 910 of the passageway 905 may be formed in the shape of a slot, as shown in FIGS. 41 and 43.

Figure 43A:
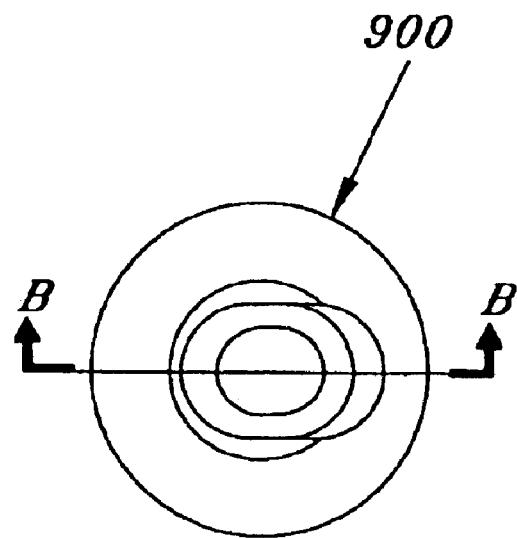
FIGS. 43A, 43B and 43C show various aspects of an alternative form of the abutment shown in FIG. 36.
Figure 43B:
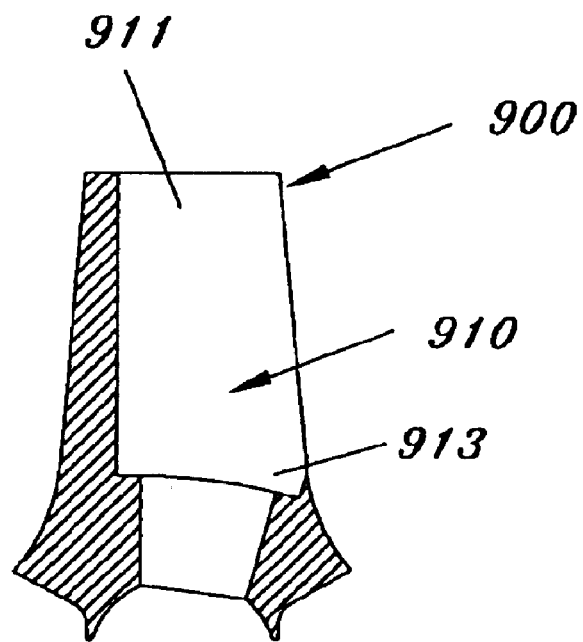
Figure 43C:
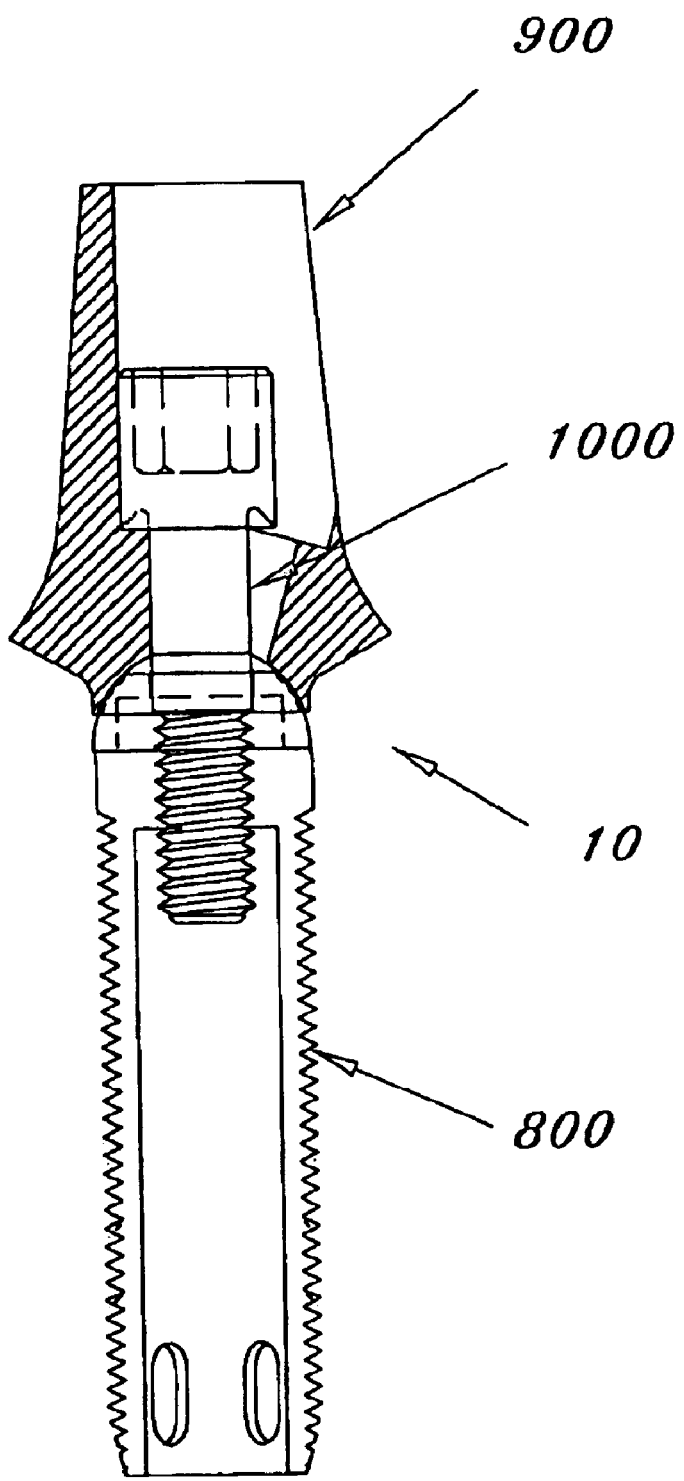

Similarly, the first stage 910 of passageway 905 might also take the form of only a portion of the slot shown in FIGS. 41 and 43. Thus, as is shown in FIGS. 43A, 43B and 43C, the first stage 910 of passageway 905 might comprise an axial bore portion 911 having side slot portion 913 extending generally radially outwardly therefrom. If desired, first stage 910 of passageway 905 might extend out the side wall of abutment 900, as shown in FIGS. 43A, 43B and 43C. Such an arrangement may be desirable inasmuch as it permits the abutment 900 to be oriented at an increased angle relative to the vertical axis of implant fixture assembly 800.

Fixation screw 1000 (FIGS. 36 and 44–46) is used to attach abutment 900 to implant fixture assembly 800. Fixation screw 1000 generally comprises a threaded distal portion 1005, a cylindrical intermediate portion 1010, and an enlarged cylindrical proximal portion 1015. A hexagonally-shaped recess 1017 is formed in the fixation screw's cylindrical proximal portion 1015, whereby the fixation screw may be rotated, e.g., by a driver. A relatively sharp edge rim 1020 (FIG. 44) is formed at the distal end of proximal portion 1015. The fixation screw's edge rim 1020 engages the abutment's annular shoulder 925 (FIGS. 42 and 46) so as to lock abutment 900 in the desired position relative to implant fixture assembly 800. In this respect it is to be appreciated that the laterally-widening first stage 910 (FIG. 42) of the abutment's multi-stage bore 905 accommodates the head of fixation screw 1000 as abutment 900 is moved off axis relative to implant fixture assembly 800.

Dental implant 10 is intended to be used in substantially the same way as the dental implant 5 described above. More particularly, an opening is first formed in the patient's gingiva, and then a hole is formed in the patient's jaw bone. In accordance with the present invention, the hole is formed in the patient's jaw bone so as to substantially optimize the safe and secure attachment of implant fixture assembly 800 to the jaw bone. Then implant fixture assembly 800 is screwed, distal end first, into the jaw bone. Next, the distal end of abutment 900 is brought into engagement with the proximal end 815 of implant fixture assembly 800, and fixation screw 1000 is used to loosely secure the two members together. More particularly, fixation screw 1000 is initially only loosely threaded into threaded bore 825 of implant fixture assembly 800, such that abutment 900 will be held to implant fixture assembly 800, yet still be capable of being moved about relative to implant fixture assembly 800. In this respect it will be appreciated that the laterally-widening first stage 910 (FIG. 42) of the abutment's multistage bore 905 will accommodate the head of fixation screw 1000 as abutment 900 is moved off axis relative to implant fixture assembly 800. The dental practitioner then selects the precise orientation desired for abutment 900 relative to implant fixture assembly 800. In accordance with the present invention, abutment 900 is intended to be oriented so as to substantially optimize the orientation of a prosthetic tooth which will be attached to the proximal end of abutment 900. Once the proper orientation of abutment 900 has been established, fixation screw 1000 is tightened all the way down, whereupon the fixation screw's annular rim 1020 will engage the abutment's shoulder 925 and thereby force the abutment's annular rim 930 into secure engagement with selected ones of the housing's facets 835, whereby subsequent slippage of abutment 900 relative to implant fixture assembly 800 will be prevented. If it is thereafter determined that the alignment of abutment 900 needs to be adjusted, fixation screw 1000 is loosened and the process repeated. Thereafter, after the deployment of dental implant 10 has been finalized, a prosthetic tooth may be fabricated in ways well known in the art, and then attached onto abutment 900, also in ways well known in the art. It should be appreciated that the cement used to hold the prosthetic tooth onto abutment 200 will fill the multistage bore 905 and help hold fixation screw 1000 fast. In this respect it should also be appreciated that the abutment and screw are preferably formed so that the cement will be able to fill around the head of the screw, in the manner shown in FIGS. 36, 46 and 43C.

It is to be appreciated that with the dental implant 10 described above, fixation screw 1000 follows the orientation of housing 805 and not (necessarily) the orientation of abutment 900, as seen in FIG. 46.

It should also be appreciated that, if desired, tool 600 may be used to set abutment 900 on implant fixture assembly 800.

And it should be appreciated that cover screw 700, or cover screw 720, may be used in conjunction with dental implant 10, if it is desired to seal off the open proximal end of implant fixture assembly 800 during a period of healing.

In addition, it should also be appreciated that the outer surface 200A of abutment 200 (FIG. 1), and the outer surface 900A of abutment 900 (FIG. 36), are preferably formed with a profile which is tapered in the manner shown. More particularly, the profile preferably comprises a hollow ground profile which provides a concave geometry. This taper is advantageous in that it (1) provides a good path of insertion, (2) provides a good mechanical interlock with the dental prosthesis which will be mounted on the abutment, (3) permits the prosthesis to be set with the desired disposition on the abutment, i.e., it permits the prosthesis to be set at the desired angle on the abutment, and (4) provides a space for receiving a substantial quantity of luting material. In one preferred form of the invention, the outer surface 200A of abutment 200, and the outer surface 900A of abutment 900, is set at an angle of 6–12 degrees off the longitudinal axis of the prosthesis.

Furthermore, dental implant 5 might have its implant fixture assembly 100 formed without screw threads 140 formed thereon. More particularly, implant fixture assembly 100 might have some other external geometry to facilitate its fixation in the patient's jaw bone 410, e.g., it might be formed with a generally cylindrical external geometry, with an external surface configured to promote osseointegration, or carrying an external surface coating adapted to promote osseointegration. Correspondingly, dental implant 10 might have its implant fixture assembly 800 similarly formed.

It is to be understood that the present invention is by no means limited to the particular constructions herein disclosed and/or shown in the drawings, but also comprises any modifications or equivalents within the scope of the claims.

What is claimed is:

1. A dental implant comprising:

an elongate implant fixture assembly having a first end and a second end, said implant fixture assembly being adapted for attachment to a jaw bone at a first end thereof and having a first longitudinal axis;

an abutment for mounting on said second end of said implant fixture assembly, said abutment having a second longitudinal axis;

a fastener for connecting said abutment to said second end of said implant fixture assembly such that (i) said abutment is adjustably movable on said second end of said implant fixture assembly when the connection formed by said fastener is loose, and (ii) upon disposition of said second longitudinal axis of a selected angle to said first longitudinal axis, said abutment is fixedly connectable on said second end of said implant fixture assembly when the connection formed by said fastener is tight; and securement means for preventing movement of said abutment relative to said implant fixture assembly when the connection formed by said fastener is tight;

wherein said second end of said implant fixture assembly is rounded, said abutment is provided with a concave end shaped complementarily to said second end of said implant fixture assembly, and said fastener is adapted to connect said abutment to said second end of said implant fixture assembly such that said implant fixture assembly and said abutment are movable relative to one another when the connection formed by said fastener is loose, and is adapted to tightly connect said abutment to said implant fixture assembly when said connection formed by said fastener is tight; and wherein said securement means comprises a lip peripherally of said concave end of said abutment, and concentric facets on said second end of said implant fixture assembly, said facets and said lip being operative to assist in positioning of said abutment so as to dispose said second longitudinal axis at said selected angle relative to said first longitudinal axis, and to assist in holding said abutment at said selected angle on said implant fixture assembly.

2. A dental implant comprising:

an elongate implant fixture assembly having a first end a second end, said implant fixture assembly being adapted for attachment to a jaw bone at a first end thereof and having a first longitudinal axis;

an abutment for mounting on said second end of said impl fixture assembly, said abutment having a second longitudinal axis;

a fastener for connecting said abutment to said second e of said implant fixture assembly such that (i) said abutment adjustably movable on said second end of said implant fixture assembly when the connection formed by said fastener is loose, and (ii) upon disposition of said second longitudinal axis of a selected angle to said first longitudinal axis, said abutment is fixedly connectable on said second end of said implant fixture assembly when the connection formed by said fastener is tight; and securement means for preventing movement of said abutment relative to said implant fixture assembly when the connection formed by said fastener is tight;

wherein said implant fixture assembly comprises a tubular housing having external threads for said attachment to the jaw bone;

wherein said implant fixture assembly further comprises a floating nut captured in said housing at said second end thereof, said floating nut having internal threads for threaded engagement with said fastener; and wherein said securement means comprise an opening having a polygonal transverse cross-section at said second end of said housing and substantially polygonal external transverse cross-section defined by said floating nut, whereby when said fastener is tightened, at least some of the sides of said external transverse cross-section of said floating nut engage at least some of the sides of said floating nut engage at least some of the sides of said transverse cross-section of said opening at said second end of said housing.

3. A method for effecting a dental restoration, the method comprising the steps of:

attaching an implant fixture assembly to a jaw bone;

attaching an abutment to said fixture assembly by a retaining screw so as to permit tilting movement of said abutment on said implant fixture assembly;

tilting said abutment on said implant fixture assembly so as to place a longitudinal axis of said abutment at a selected angle to a longitudinal axis of said implant fixture assembly; and tightening said retaining screw so as to secure said abutment to said implant fixture assembly at said selected angle and engage securement means for preventing movement of said abutment relative to said fixture assembly;

wherein said implant fixture assembly includes a floating nut therein, and said step of attaching said abutment to said implant fixture assembly comprises advancing said threaded shank portion of said screw into said floating nut; and wherein said floating nut and said implant fixture assembly together define securement means comprising an opening having a polygonal transverse cross-section at said second end of said housing and a substantially polygonal external transverse cross-section defined by said floating nut, whereby when said fastener is tightened, at least some of the sides of said external transverse cross-section of said floating nut engage at least some of the sides of said transverse cross-section of said opening at said second end of said housing.

* * * * *